United States Patent
Konandreas et al.

(10) Patent No.: US 10,004,850 B2
(45) Date of Patent: Jun. 26, 2018

(54) SYRINGE HOLDER FOR A MOTORIZED INJECTION DEVICE

(71) Applicant: Juvaplus SA, Genève (CH)

(72) Inventors: Stefanos Konandreas, Petit-Saconnex/Genève (CH); Bernard-Pierre Legrand, Conches (CH)

(73) Assignee: JUVAPLUS SA, Geneve (CH)

( * ) Notice: Subject to any disclaimer, the term of this patent is extended or adjusted under 35 U.S.C. 154(b) by 78 days.

(21) Appl. No.: 15/078,711

(22) Filed: Mar. 23, 2016

(65) Prior Publication Data

US 2016/0279331 A1    Sep. 29, 2016

(30) Foreign Application Priority Data

Mar. 25, 2015   (CH) .......................... 431/15

(51) Int. Cl.
*A61M 5/20* (2006.01)
*A61M 5/24* (2006.01)
*A61M 5/315* (2006.01)

(52) U.S. Cl.
CPC ................ *A61M 5/20* (2013.01); *A61M 5/24* (2013.01); *A61M 5/31571* (2013.01);
(Continued)

(58) Field of Classification Search
CPC .......... A61M 5/31571; A61M 5/31576; A61M 5/31565; A61M 5/31566; A61M 5/31586; A61M 2005/31588; A61M 2205/586
See application file for complete search history.

(56) References Cited

U.S. PATENT DOCUMENTS

| | | |
|---|---|---|
| 4,710,178 A | 12/1987 | Leonard et al. |
| 6,159,161 A | 12/2000 | Hodosh |
| 2014/0039405 A1* | 2/2014 | Konandreas ........ A61M 5/3158 604/193 |

FOREIGN PATENT DOCUMENTS

| | | |
|---|---|---|
| CH | 600893 A5 | 6/1978 |
| EP | 2 689 793 A1 | 1/2014 |

(Continued)

OTHER PUBLICATIONS

The Editors of Encyclopaedia Britannica. "Lever". Encyclopaedia Britannica. Dec. 11, 2014. https://www.britannica.com/technology/lever.*

(Continued)

*Primary Examiner* — Andrew Gilbert
*Assistant Examiner* — Courtney Frederickson
(74) *Attorney, Agent, or Firm* — Christensen, Fonder, Dardi & Herbert PLLC; John Fonder

(57) ABSTRACT

A syringe holder for a motorized injection device, the syringe holder being adapted to receive a receptacle intended to contain a fluid or viscous substance, preferably a disposable refillable receptacle or a syringe, as well as being adapted to be mounted on the motorized injection device such that the motorized injection device enables a part or all of the fluid or viscous substance contained in said receptacle to be expelled. The syringe holder includes a first activator portion to control a predefined function of the motorized injection device. The syringe holder is distinguished in that it comprises a second activator portion to control said predefined function of the motorized injection device independently from the first activator portion.

7 Claims, 3 Drawing Sheets

(52) U.S. Cl.
CPC .... *A61M 5/31576* (2013.01); *A61M 5/31586* (2013.01); *A61M 5/31565* (2013.01); *A61M 5/31566* (2013.01); *A61M 2005/31588* (2013.01); *A61M 2205/586* (2013.01)

(56) References Cited

FOREIGN PATENT DOCUMENTS

| KR | 10-2013-0115542 A | 10/2013 |
|----|-------------------|---------|
| WO | WO 96/25965 A1 | 8/1996 |
| WO | WO 2013/045617 A1 | 4/2013 |

OTHER PUBLICATIONS

Teoxane SA, TeosyalPen—for the fine art of precision, internet, Jan. 1, 2015, www.teosyalpen.com (7 pgs.).

* cited by examiner

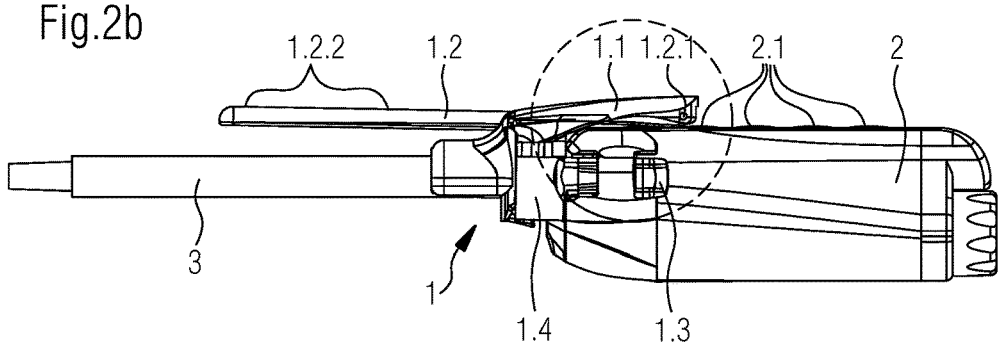
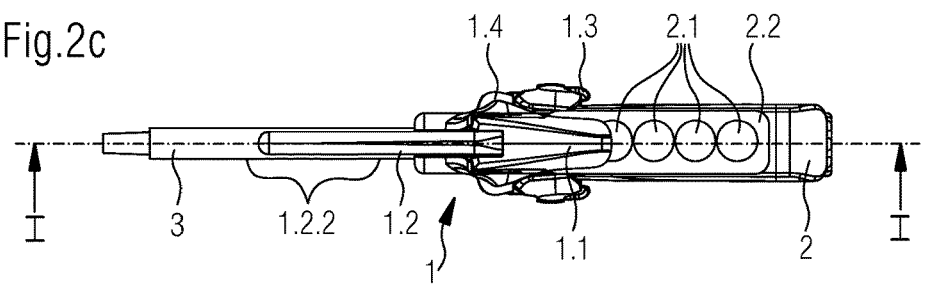
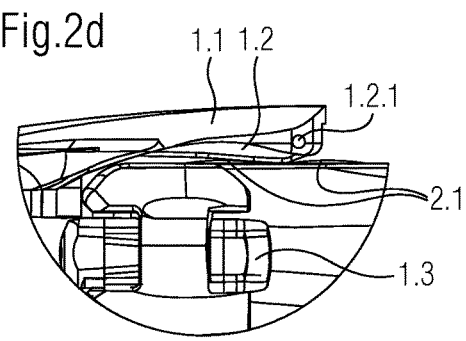
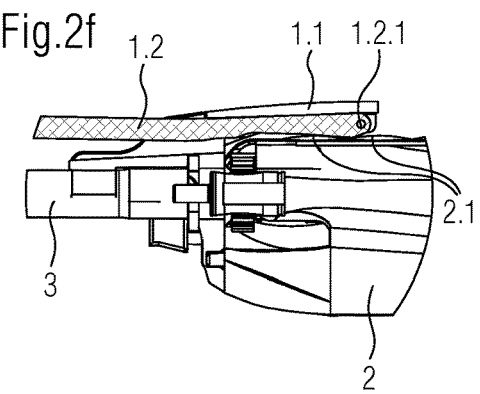
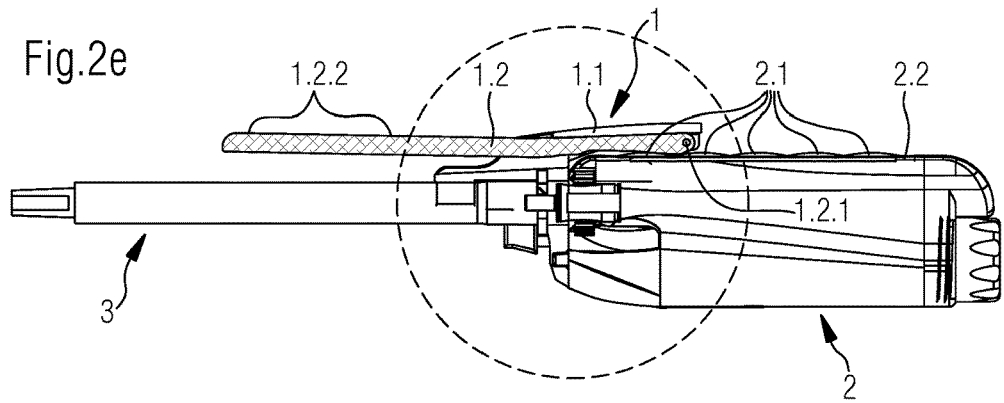

SYRINGE HOLDER FOR A MOTORIZED INJECTION DEVICE

RELATED APPLICATION

The present application claims priority to Swiss Patent Application No. 00431/15, filed Mar. 25, 2015, the disclosure of which is hereby incorporated by reference herein in its entirety.

FIELD OF THE INVENTION

The object of the present invention is a syringe holder for a motorized injection device, the syringe holder being adapted to receive a receptacle intended to contain a fluid or viscous substance, preferably a disposable refillable receptacle or a syringe, as well as being adapted to be mounted on said motorized injection device such that the motorized injection device enables at least a part or even all of the fluid or viscous substance contained in said receptacle to be expelled, the syringe holder comprising a first activation means allowing to control a predefined function of said motorized injection device. The present invention also relates to a motorized injection device adapted to receive such a syringe holder.

BACKGROUND OF THE INVENTION

In this context, it should be noted that European patent application EP 2 689 793 discloses an injection device equipped with a power source, a motor system powered by said power source and driving a first piston specific to the motor system, and a syringe holder adapted to be mounted on said motor system and adapted to receive different types of syringes or receptacles. Thus, once the motor system of the injection device is activated, said first piston enables a product contained in the syringe, respectively in the receptacle, to be ejected, i.e., to be injected into the body of a patient, by pressing on the second piston specific to the syringe, respectively on the receptacle housed in the syringe holder, in a manner that is controlled and effortless to the user.

This injection device was designed to facilitate the work of the practitioner who can focus his attention and his effort on injecting the product and on the patient instead of having to devote a significant part of his attention on handling a conventional type syringe as well as having to exert, depending on the viscosity of the product to be injected, greater or lesser force on the piston of the syringe by manually pressing thereon. The device simultaneously enables most conventional syringes to be used, given that it is equipped with said syringe holder that is used to mount syringes on the housing of the motor system of the injection device. Not only can the device be used in combination with several types of syringes prefilled with a product to be injected, but also with syringes or even other types of receptacles that the practitioner has to fill immediately before use. In fact, certain applications require the product to be prepared just before use, such as, for example, botulinum toxin which is widely used in cosmetic medicine.

To obtain optimal performance of the injection device, it is important that the practitioner has optimal visibility of the receptacle containing the product to be injected, that he has optimal handling at the ergonomic level, and that he can operate the device without too much effort, given that the operation that he must perform often requires great precision, particularly in the field of cosmetic medicine. Whereas said injection device according to document EP 2 689 793 is already designed to reduce the effort required from the practitioner, given that it has a motor system enabling said first piston to be driven and thus preventing the practitioner from providing the force necessary to eject the product of said receptacle himself, practical experience has shown that certain applications exist for which the syringe holder mentioned above does not take full advantage of the injection device. In fact, on the one hand, situations exist where the practitioner would wish to use even less effort compared to that offered by the syringe holder of the above mentioned system. On the other hand, situations also exist where the ergonomics of this syringe holder and the resulting visibility are not ideal.

SUMMARY OF THE INVENTION

For the reasons described above, the prior art currently does not comprise a support means that can be adequately used in combination with the above mentioned injection device and that would enable the practitioner to have increased comfort compared to the known syringe holder mentioned above.

Therefore, an object of the present invention is to remedy the above mentioned disadvantages and to make available to practitioners using the motorized injection devices mentioned above a syringe holder adapted to be mounted on this type of injection device and to further reduce the effort required to activate the device, respectively to then inject the product contained in the receptacle housed in the syringe holder. Another object of the present invention is to realize this syringe holder, i.e., the means to support a receptacle supposed to be mounted on the housing of a motorized injection device, while improving the visibility onto the receptacle containing the product to be injected as well as the handling of the injection device. Still another object of the present invention is to realize this support means in a simple manner, at a moderate cost, as well as in such a way that it is reliable and flexible during use. Another object of the present invention is to realize an injection device that is ideally suitable for this type of syringe holder.

For this purpose, the present invention proposes a syringe holder, respectively a motorized injection device of the above mentioned type that is distinguished by the characteristics stated in the claims. In particular, a syringe holder according to the present invention is distinguished by the fact that it comprises a second activation means or portion allowing said predefined function of the motorized injection device to be controlled independently from the first activation means or portion, and the motorized injection device is distinguished by the fact that it comprises at least one activation button positioned in specific manner on the upper surface of said motorized injection device.

By these measures, the syringe holder allows an optimal use of a motorized injection device of the above mentioned type because it further reduces the effort necessary by the practitioner to operate the device, respectively to then inject the product contained in the receptacle housed in the syringe holder, given that even the activation can thereby be carried out with minimal effort by using the second activation means, the force necessary to eject the product out of the receptacle being anyway provided by the motor system of the device. In addition, this syringe holder simultaneously improves the handling of the motorized injection device, given that the practitioner can choose to use the first and/or the second activation means situated on the syringe holder, as well as, for the same reason, the visibility onto the receptacle containing the product to be injected. Thus, a support means is obtained that is optimally suitable for use in combination with a motorized injection device, this syringe holder nevertheless being of simple construction, inexpensive for fabrication, as well as robust and reliable during use.

Other characteristics, as well as the corresponding advantages, will become apparent from the various claims, as well as from the description presenting the invention in further detail below.

BRIEF DESCRIPTION OF THE DRAWINGS

The attached drawings schematically represent, by way of example, an embodiment of the invention.

FIG. 2b is a schematic side view of the syringe holder of FIG. 2a including said motorized injection device as well as the receptacle; FIG. 2c is a schematic top view of the syringe holder of FIG. 2a including said motorized injection device as well as the receptacle; FIG. 2d is an enlargement of part of FIG. 2b showing the syringe holder according to the present invention in further detail; FIG. 2e is a longitudinal section, in which some parts are illustrated in transparent view to aid understanding, across the syringe holder, the motorized injection device, as well as the receptacle along line I-I indicated in FIG. 2c; FIG. 2f is an enlargement of part of FIG. 2e showing the syringe holder according to the present invention in further detail.

DETAILED DESCRIPTION OF THE INVENTION

Figure 1:
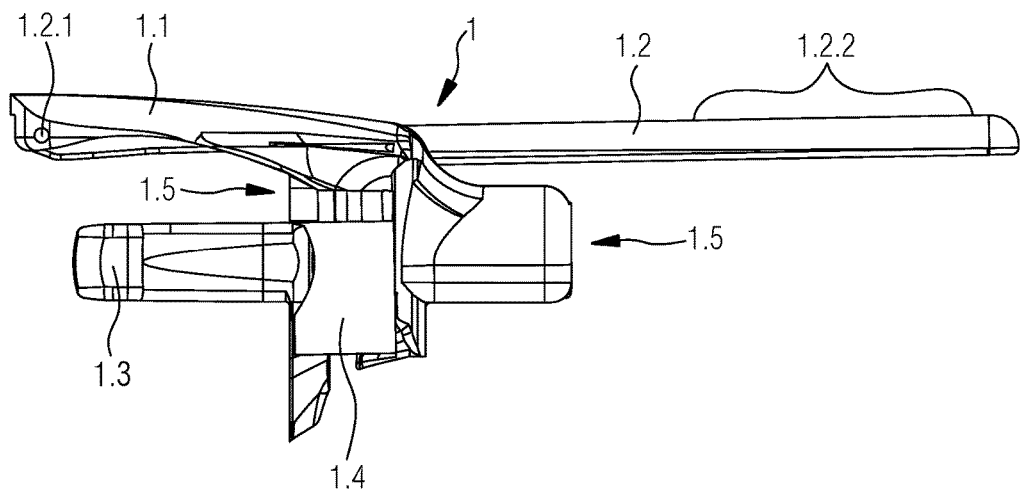
FIG. 1 represents a schematic side view of a syringe holder according to an embodiment of the present invention adapted to be mounted on a motorized injection device.

The invention will now be described in detail with reference to the attached drawings illustrating, by way of example, an embodiment of the invention.

An embodiment of the present invention relates to a syringe holder 1 for a motorized injection device 2, the syringe holder 1 being adapted to receive a receptacle 3 intended to contain a fluid or viscous substance, or even generally a product used in general medicine or in cosmetic medicine for injection into the body of a patient, as well as being adapted to be mounted onto said motorized injection device 2. The motorized injection device 2 allows to eject at least part or even all of the product, respectively the fluid or viscous substance contained in said receptacle 3, by comprising a motor system powered by a power source and driving a first piston specific to the motor system, said first piston applying on a second piston specific to the receptacle 3, respectively to the syringe housed in the syringe holder 1. Such a motorized injection device 2 as well as a corresponding receptacle 3, often taking the form of a conventional syringe or, preferably, of a disposable refillable receptacle, are described in detail in the document EP 2 689 793 which is incorporated into the present description by reference in its entirety, these elements therefore not being described in more detail in the following. The syringe holder 1, such as known in the prior art and also disclosed in particular in document EP 2 689 793, comprises a first activation means, also referred to as a first activator or first activation portion 1.1 allowing to control a predefined function of said motorized injection device 2.

This predefined function normally consists of starting and stopping the motor of the motorized injection device 2 and in this case, following actuation of said first activation means 1.1 of the syringe holder 1, this means applies on, when the syringe holder 1 is mounted on the motorized injection device 2, a corresponding control button 2.1 of said device 2, this button 2.1 controlling the starting and stopping of the first piston of the motorized injection device 2. Thus, following a first actuation of said first activation means 1.1 of the syringe holder 1, the motor of device 2 drives the first piston specific to the motor system which in turn applies on the second piston specific to the syringe, respectively to the receptacle 3, housed in the syringe holder 1. The product contained in the receptacle, respectively the syringe, is then ejected from the receptacle, respectively injected into the body of a patient. A second actuation of said first activation means 1.1 of the syringe holder 1 then allows to stop the motor of device 2, respectively to stop the first piston specific to the motor system as well as the second piston specific to the syringe, such that the injection of the product into the body of the patient also stops. Preferably, the button 2.1 controlling the starting and stopping of the first piston of the motorized injection device 2 is arranged such that pressing on this button 2.1 causes the product to be injected during all the time it is actuated and causes the injection of the product to be stopped when the pressing on the control button 2.1 is released. However, the predefined function may also consist of another function.

In fact, the syringe holder 1 for a motorized injection device 2 according to the present invention comprises a main body 1.4 adapted to receive a receptacle 3, such as a disposable refillable receptacle or a conventional syringe, by comprising an opening 1.5 extending axially through the syringe holder 1 in which the receptacle 3 may be inserted, which is schematically illustrated in FIG. 1. In addition, the syringe holder 1 is obviously adapted to be mounted on the motorized injection device 2, for example by using lateral fixation tabs 1.3 or any other similar fixation means. Given that the first piston specific to the motor system of the injection device 2 may traverse said opening 1.5 in the syringe holder 1 to penetrate into the inside of receptacle 3, in order to bear on the second piston of receptacle 3, the motorized injection device 2 allows to eject at least part or even all of the fluid or viscous substance contained in said receptacle 3, once the syringe holder 1 with a receptacle 3 containing a product has been mounted on the device 2. Details and alternative techniques relating to the fixation of receptacle 3 in the syringe holder 1 as well as the fixation means and assembly of the syringe holder 1 on the motorized injection device 2 will not be discussed in the following, given that, first, this information is found in document EP 2 689 793 and, second, it has no major influence on the present invention.

This invention mainly resides in the fact that such a syringe holder 1 comprises a second activation means, also referred to as a second activator or second activation portion, 1.2 also allowing said predefined function of the motorized injection device 2 to be controlled independently from the first activation means 1.1. As illustrated schematically and by way of example in the side view of FIG. 1, this second activation means 1.2 of the syringe holder 1 is realized, preferably, by an actuation lever 1.2 articulated on the first activation means 1.1. The hinge pin 1.2.1 may be made by a pin fixed to the first activation means 1.1 and housed in a through hole of the actuation lever 1.2 or, conversely, by a pin fixed to the actuation lever 1.2 whose ends are housed in corresponding holes formed in the lower part of the free end of said first activating means 1.1 of the syringe holder 1, this free end being directed towards the proximal end of the motorized injection device 2. The hinge pin 1.2.1 may also be made by cylindrical or conical projections formed in one piece with the actuation lever 1.2, these projections being housed in the corresponding holes formed in said free end of said activation means 1.1 of the syringe holder 1 or, conversely, by the projections formed in one piece with the first activation means 1.1, these projections being housed in corresponding holes formed in the actuation lever 1.2.

Figure 2A:
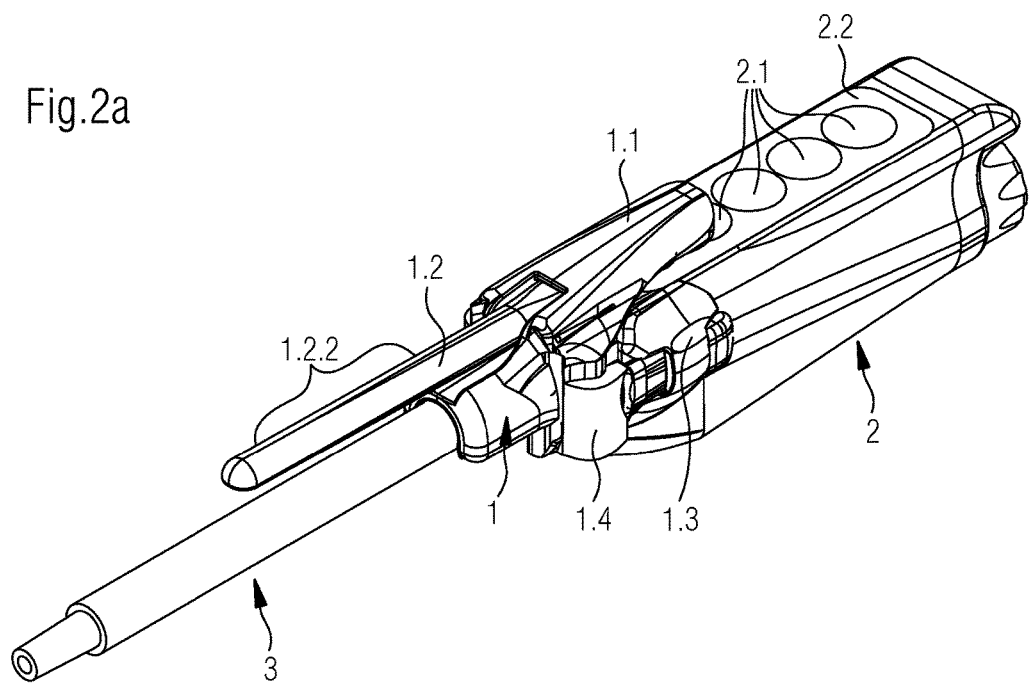
FIG. 2a shows a schematic perspective view of a syringe holder according to an embodiment of the present invention in a state mounted on a motorized injection device as well as accommodating a receptacle containing a product intended to be injected into the body of a patient.

The free end of the lever forming the second activation means 1.2 of the syringe holder 1 is directed towards the distal end of the receptacle 3 mounted in the syringe holder 1, such that this actuation lever 1.2 extends substantially parallel to the receptacle 3, by presenting an activation zone 1.2.2 along which the user of the device may press as he wishes, particularly depending on the size of his hand as well as on the manner in which he wishes to hold the motorized injection device 2 including the syringe holder 1 and the syringe 3 installed in the latter. The proximal end of the lever forming the second activation means 1.2 of the syringe holder 1 articulated to the first activation means 1.1 is assembled under the latter, like also illustrated in FIGS. 2*a* and 2*b*. It is apparent in particular from FIG. 2*d*, which shows in an enlarged manner a detail from FIG. 2*b*, that in an assembled state on the motorized injection device 2, a part of the lever forming the second activation means 1.2 of the syringe holder 1 close to the hinge pin 1.2.1 is superimposed on the control button 2.1 of the motorized injection device 2 allowing said predefined function of the device 2 to be activated and stopped. In turn, the first activation means 1.1 is superimposed on the proximal end of the lever forming the second activation means 1.2 of the syringe holder 1 covering said control button 2.1 of the motorized injection device 2. Thus, this control button 2.1 of the motorized injection device 2 allowing to activate and to stop said predefined function of the device 2 may be activated either directly by the second activation means 1.2 of the syringe holder 1, by pressing on a given location situated along its activation zone 1.2.2, or indirectly by pressing on the first activation means 1.1 of the syringe holder 1 which displaces the second activation means 1.2 situated under its lower surface and articulated at its free end. The second activation means 1.2 of the syringe holder 1 is, preferably, maintained in its rest position, in which it does not bear on the control button 2.1 of the motorized injection device 2 allowing said predefined function of device 2 to be activated and stopped, by a pretensioned spring situated between the first activation means 1.1 and the second activation means 1.2, by elastic deformation of the lateral feet connecting the first activation means 1.1 to the main body 1.4, between which is housed the second activation means 1.2, or by any other suitable means.

Preferably, the actuation lever 1.2 is formed by a rod with a total length of approximately 40 mm to 90 mm, preferably 50 mm to 70 mm, such that the free end of the rod exceeding the first activation means 1.1 should cover less than half of the length of the receptacle 3, respectively of the syringe. Its end directed towards the distal end of the receptacle 3 will thus be approximately situated in the second quarter or in the second third of the total length of the motorized injection device 2 including the syringe holder 1 and the syringe 3. Consequently, the actuation force of said predefined function required by the second activation means 1.2 of the syringe holder 1 is less than the actuation force required by the first activation means 1.1 of syringe holder 1, because the favorable lever effect procured by the multiplication of the pressing force depending on the exact location where the user presses along the activation zone 1.2.2 of the second activation means 1.2 allows to activate said control button 2.1 by requiring practically no effort on the part of the user. In addition, the user can, by choosing the exact location where he presses along the activation zone 1.2.2 of the second activation means 1.2 of the syringe holder 1, gradually choose the effort required to activate the predefined function, which is more specifically apparent from the cross-sectional views in FIGS. 2*e* and 2*f*.

As relating to the first activation means 1.1, it should first be noted that it is arranged on the main body 1.4 of the syringe holder 1 so as to be directed towards the end of the syringe holder 1 supposed to be mounted on said motorized injection device 2. Preferably, the first activation means 1.1 forms a protective surface covering, when the syringe holder 1 is mounted on the motorized injection device 2, at least part of the control buttons 2.1 positioned on the upper surface 2.2 of said motorized injection device 2, in order to prevent any involuntary actuation of the control buttons 2.1 placed under this protective surface. Furthermore, the first activation means 1.1 may advantageously be formed in one piece with the main body 1.4 of the syringe holder 1, with which it may specifically be connected by lateral legs as illustrated, for example, in FIGS. 2*a* and 2*c*. In this case, the first activation means 1.1 is actionable by elastic deformation of its proximal end and of said lateral legs, so as to be adapted to bear, through the second activation means 1.2, on one of the control buttons 2.1 positioned on the upper surface 2.2 of said motorized injection device 2 in order to control said predefined function of said motorized injection device 2.

Figure 3A:
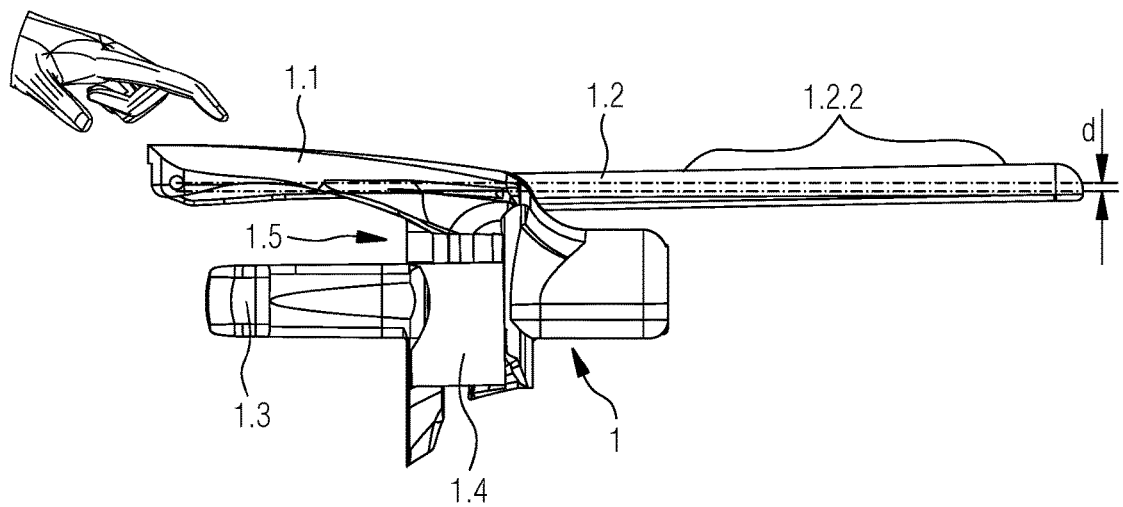
FIG. 3a illustrates, by a schematic side view of a syringe holder according to an embodiment of the present invention, the control of a motorized injection device through the operation of the first activation means of the syringe holder.
Figure 3B:
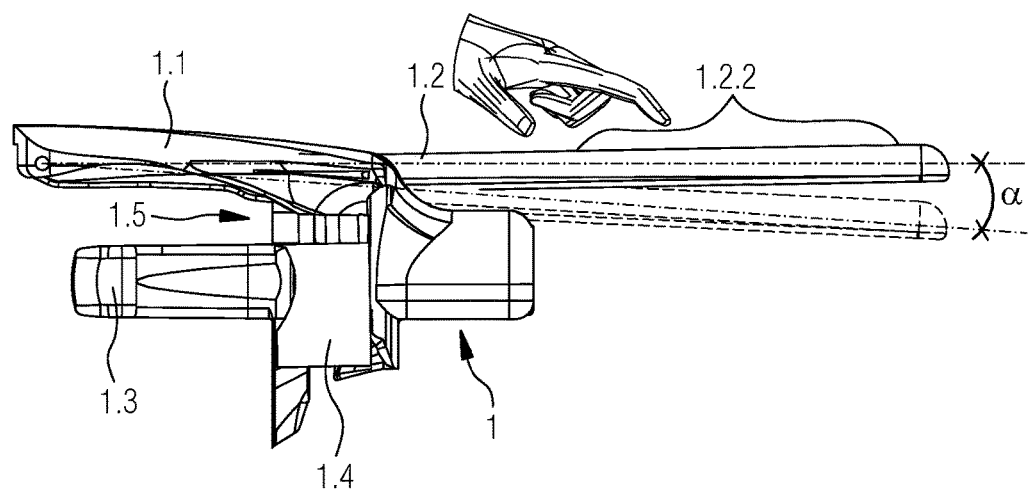
FIG. 3b illustrates, by a schematic side view similar to FIG. 3a of a syringe holder according to the present invention, the control of a motorized injection device through the operation of the second activation means of the syringe holder.

In view of the above description of the structure of a syringe holder according to the present invention, the operation of this type of support or support means in combination with a motorized injection device 2 is easily understood. In fact, as illustrated in FIG. 3*a* by a schematic side view of a syringe holder according to the present invention, it is possible to control a motorized injection device 2 of the type mentioned in the introduction by actuating the first activation means 1.1 of the syringe holder 1, simply by pressing on the latter. Alternatively, as illustrated in FIG. 3*b* by a schematic side view similar to FIG. 3*a*, it is also possible to control such a motorized injection device 2 by actuation of the second activation means 1.2 of the syringe holder 1, also simply by pressing on the activation zone 1.2.2 of the latter, this requiring both a lower and more controllable actuation force. Also, it is apparent from FIGS. 3*a* and 3*b* that, by using the first activation means 1.1 of the syringe holder 1, the control lever 1.2 is displaced substantially parallel in relation to its rest position, i.e. by a distance d, until it bears on the control button 2.1 positioned on the upper surface 2.2 of said motorized injection device 2 controlling said predefined function, while, by using the second activation means 1.1 of the syringe holder 1, the actuation lever 1.2 is angularly displaced by an angle α around the hinge pin 1.2.1, also until it bears on the control button 2.1 of the motorized injection device 2.

It remains to be noted that the present invention also relates to a motorized injection device 2 adapted to receive such a syringe holder 1, this device 2 comprising a predefined number of control buttons 2.1 positioned on its upper surface and controlling the various functions of the motorized injection device 2. In particular, in a motorized injection device 2 according to the invention, at least part of the control buttons 2.1 controlling the functions affecting the safety of the injection device 2 are positioned on the upper surface 2.2 of the device such as to be covered, once syringe holder 1 is mounted on the motorized injection device 2, by the protective surface formed by the first activation means 1.1 of the syringe holder 1. In particular, the control buttons 2.1 controlling the functions affecting the safety of the device and positioned on the upper surface 2.2 of the device such as to be covered, when the syringe holder 1 is mounted on the motorized injection device 2, by the protective surface formed by said first activation means 1.1 of the syringe holder 1 may consist of the start and stop button of the motorized injection device 2, the start and stop button of the first piston of the motorized injection device 2, the zero reset button of the first piston of the motorized injection device 2, and/or the reset button for certain parameters of the motorized injection device 2. In such a motorized injection device 2, these control buttons 2.1 are therefore arranged on the upper surface 2.2 of the device 2 in an order chosen and adjusted according to the practical application for which the device is intended. For example, a favorable arrangement of the control buttons 2.1 controlling the various functions of the motorized injection device 2 may consist of placing, in order and starting at the distal end of the device 2, first the zero reset button of the first piston of the motorized injection device 2, then the start and stop button of the first piston of the motorized injection device 2, followed by buttons controlling the product injection rate, i.e. the rate of displacement of the first piston of the motorized injection device 2 and/or still other control buttons, to end with the start and stop button of the motorized injection device 2. This latter button and/or the reset button for certain parameters of the motorized injection device 2 may also be placed in the first or in the second position counting from the distal end of the device 2. In this way, depending on the length of the protective surface formed by the first activation means 1.1 of the syringe holder 1, the first control button or buttons 2.1 on the distal end of the device 2 are only actionable when the syringe holder 1 is removed from the motorized injection device 2, thus preventing any involuntary actuation of these buttons while the syringe holder 1 is mounted on the motorized injection device 2, and, in particular, during operation of device 2, while the control button 2.1 controlling the predefined function and situated under the control zone of the first activation means 1.1 may be controlled, as explained above, either by the first activation means 1.1 or by the second activation means 1.2 of the syringe holder 1.

In view of the explanations above, it is obvious that a syringe holder according to the invention enables optimal use of a motorized injection device of the type mentioned in the introduction while remaining compatible with any type of receptacle or syringe. In particular, such a syringe holder further reduces the effort necessary on the part of the user to operate the injection device, respectively to then inject the product contained in the receptacle housed in the syringe holder, bearing in mind that the operation of the desired function thereby can be carried out with minimal effort by using the second activation means and that the force necessary to inject the product into the body of the patient is in any case provided by the motor system of the motorized injection device. In addition, the user therefore may dose the quantity of product injected into the patient more accurately and is able to hold the motorized injection device like a fountain pen. In addition, it enables the user to choose the manner in which he would like to control the motorized injection device, with either the first or with the second activation means, thus offering greater flexibility to practitioners. This activation system thus allows both a very gentle operation thanks to the favorable lever effect and an actuation on the central part of the whole system consisting of three separate parts mounted one on the other, i.e., a receptacle housed in the syringe holder that is mounted on the housing of the motorized injection device. At the same time, this improves the handling of the motorized injection device, because the choice of using the first and/or the second activation means situated on the syringe holder enables the practitioner to also choose the ergonomic grip most which is appropriate for him. Furthermore, this also improves the visibility with respect to the receptacle containing the product to be injected, because there is no more a housing with an unfavorable ergonomic effect but a reduction to a minimum in terms of syringe holder dimensions, thus allowing better visibility for direct reading on the syringe, in terms of the quantity of product that it still contains and, above all, on the patient. The syringe holder is therefore optimally suited for use in combination with such a motorized injection device. In addition, the syringe holder is of simple sturdy construction and robust, inexpensive to produce, and reliable in operation.

The invention claimed is:

1. A syringe holder for a motorized injection device, the syringe holder being adapted to receive a receptacle intended to contain a fluid or viscous substance, as well as being adapted to be mounted on said motorized injection device, such that the motorized injection device enables at least a part or even all of the fluid or viscous substance contained in said receptacle to be expelled, the syringe holder comprising a first activation portion comprising a first lever directed towards an end of the syringe holder, the syringe holder configured to be mounted on said motorized injection device and allowing control of a predefined function of said motorized injection device, wherein the syringe holder comprises a second activation portion allowing control of said predefined function of the motorized injection device independently from the first activation portion;

wherein said second activation portion of the syringe holder comprises a second lever articulated on said first activation portion; and wherein a free end of said second lever forms the second activation portion of the syringe holder and is directed towards a distal end of the receptacle mounted in the syringe holder.

2. The syringe holder according to claim 1, wherein an actuation force of said predefined function required by the second activation portion of the syringe holder is less than an actuation force required by the first activation portion of the syringe holder.

3. The syringe holder according to claim 1, wherein said first activation portion forms a protective surface covering when the syringe holder is mounted on the motorized injection device, said motorized injection device including control buttons positioned on an upper surface of said motorized injection device.

4. The syringe holder according to claim 3, wherein said first activation portion is formed in one piece with a main body of the syringe holder and is actionable by deformation so as to be adapted to bear on one of the control buttons positioned on the upper surface of said motorized injection device in order to control said predefined function of said motorized injection device.

5. The syringe holder according to claim 1, wherein the receptacle is a disposable refillable receptacle or a syringe.

6. A control interface for a motorized injection device adapted to receive the syringe holder according to claim 1, the control interface for the motorized injection device comprising a predefined number of control buttons positioned on an upper surface of the motorized injection device and controlling functions of the motorized injection device, wherein at least one of the control buttons controlling functions affecting safety of the motorized injection device is positioned on the upper surface of the motorized injection device such as to be covered, when the syringe holder is mounted on the motorized injection device, by a protective surface formed by said first activation portion of the syringe holder.

7. The control interface of a motorized injection device according to claim 6, wherein the at least one of the control buttons controlling functions affecting the safety of the motorized injection device and positioned on the upper surface of the device such as to be covered, when the syringe holder is mounted on the motorized injection device, by the protective surface formed by said first activation portion of the syringe holder is selected from the group consisting of a start and a stop button of the motorized injection device, a start and stop button of a first piston of the motorized injection device, a zero reset button of the first piston of the motorized injection device, and a reset button of the motorized injection device.

* * * * *